US009198988B2

(12) United States Patent
Huang et al.

(10) Patent No.: US 9,198,988 B2

(45) Date of Patent: Dec. 1, 2015

(54) NANOPARTICULATE MANGANESE MRI CONTRAST AGENTS

(75) Inventors: Songping D. Huang, Kent, OH (US); Anatoly K. Khitrin, Kent, OH (US); Vindya S. Perera, Kent, OH (US); Murthi S. Kandanapitiye, Kent, OH (US)

(73) Assignee: Kent State University, Kent, OH (US)

( * ) Notice: Subject to any disclaimer, the term of this patent is extended or adjusted under 35 U.S.C. 154(b) by 58 days.

(21) Appl. No.: 13/979,685

(22) PCT Filed: Aug. 29, 2011

(86) PCT No.: PCT/US2011/001520

§ 371 (c)(1), (2), (4) Date: Jul. 15, 2013

(87) PCT Pub. No.: WO2012/108856

PCT Pub. Date: Aug. 16, 2012

(65) Prior Publication Data

US 2013/0302256 A1 Nov. 14, 2013

Related U.S. Application Data

(60) Provisional application No. 61/462,804, filed on Feb. 8, 2011.

(51) Int. Cl.

| | |
|---|---|
| ***A61B 5/055*** | (2006.01) |
| ***A61K 49/18*** | (2006.01) |
| ***A61K 49/08*** | (2006.01) |
| *A61K 33/32* | (2006.01) |

(52) U.S. Cl.

CPC ............ *A61K 49/1851* (2013.01); *A61K 49/08* (2013.01); *A61K 49/1821* (2013.01); *A61K 33/32* (2013.01)

(58) Field of Classification Search

CPC .................................................... A61K 49/06

See application file for complete search history.

(56) References Cited

U.S. PATENT DOCUMENTS

| | | | |
|---|---|---|---|
| 2010/0133487 | A1 | 6/2010 | Kawamoto et al. |
| 2010/0215587 | A1 | 8/2010 | Huang et al. |
| 2010/0254912 | A1 | 10/2010 | Huang et al. |

OTHER PUBLICATIONS

Okubo et al. (J. Phys. Chem. Lett. 2010, 1, 2063-2071).*

Lebel (2010) Advances in Magnetic Resonance Imaging of the Human Brain at 4.7 Tesla, Doctor of Philosophy Biomedical Engineering, p. 1-168.*

R Martinez-Garcia, et al., "Magnetic interaction between manganese (2+) atoms through aquo bridges and bifurcated cyano groups", Journal of Physics: Condensed Matter, Jan. 15, 2007, 1-11,IOP Publishing Ltd., UK; online at stacks.iop.org/JPhysCM/19/056202.

* cited by examiner

*Primary Examiner* — Michael G Hartley

*Assistant Examiner* — Melissa Perreira

(74) *Attorney, Agent, or Firm* — Hudak, Shunk & Farine Co. LPA

(57) ABSTRACT

This invention discloses a synthetic procedure for preparing nanoparticulate materials of various metal cyanide compounds containing manganese(II) ions in the crystal lattice with the surfaces coated by a hydrophilic compound, and their use as MRI contrast agents with high sensitivity, long blood circulation half lives and low toxicity at low-field and high field MR scanners.

18 Claims, 5 Drawing Sheets

Schematic structures of the common MR contrast agents with one coordinated water molecule omitted from each structure for clarity Crystal structure of KMn[$Fe^{III}$(CN)6].

Color Code: White = carbon;
small grey = nitrogen;
medium grey = iron;
large grey = potassium and
black = manganese.

The $Mn^{2+}$ ion leaching results under different conditions.

The proton $T_1$ (top) and $T_2$ (bottom) relaxation rate versus concentration of $Mn^{2+}$ ion at 11.7 T.

The proton $T_1$ (top) and $T_2$ (bottom) relaxation rate versus concentration of $Mn^{2+}$ ion at 7.0 T.

NANOPARTICULATE MANGANESE MRI CONTRAST AGENTS

CROSS-REFERENCE

This application claims the priority filing date of U.S. Provisional Application Ser. No. 61/462,804 filed Feb. 8, 2011, herein fully incorporated by reference.

FIELD OF THE INVENTION

Nanoparticles of various metal cyanide compounds containing manganese(II) ions in the crystal lattice having very low release of free $Mn^{2+}$ ions, very low cyanide toxicity and high relaxivity values are suitable as MRI contrast agents. The nanoparticles are surface modified with a water-soluble and biocompatible polymer, have long blood circulation half lives, and can be used at low concentrations with low- and high-magnetic field scanners to enhance magnetic resonance imaging (MRI) contrast.

BACKGROUND OF THE INVENTION

From the entire periodic table, there are only a few elements with a stable and biocompatible oxidation state and a high number of unpaired electrons that are considered suitable for image enhancement applications in magnetic resonance imaging (MRI). These include Mn(II) (HS; S=5/2), Fe(III) (HS; S=5/2) and Gd(III) (S=7/2). The MRI signal intensity (SI) from different body tissues varies with the content of water protons present in the tissue and with both the longitudinal ($T_1$) and transverse ($T_2$) relaxation times of those protons. In some cases, the variation of water content in different tissues is sufficient to produce image contrast. In other cases, it is necessary to use a contrast agent to enhance the image contrast. Chemical compounds that can change the relaxation times, either $T_1$ or $T_2$, within a tissue are routinely used as contrast agents in MRI in the medical diagnosis of diseases and/or organ functions in the human body.

Clinical MRI contrast agents can be divided into two classes, $T_1$ agents and $T_2$ agents. A $T_1$ or positive contrast agent shortens the longitudinal relaxation time ($T_1$) of water protons, and can brighten regions where the agent is present. Conversely, a $T_2$ or negative contrast agent reduces the transverse relaxation time ($T_2$) of water protons, and produces darkened spots in the tissues reached by the agent when a residual transverse magnetization is used in a spin-echo experiment.

The majority of the $T_1$ contrast agents have been developed from the use of the paramagnetic $Gd^{3+}$ ion chelated by various low molecular weight polyaminopolycarboxylate ligands. The high electronic spin ($4f^7$, S=7/2, 7.9 BM), coupled with a symmetric electronic ground state ($^8S_{7/2}$) and slow electronic relaxation ($10^{-9}$ s), gives Gd(III) unique nuclear-magnetic properties for enhancing $T_1$-relaxation of protons from bulk water. Currently, there are nine commercial $T_1$ agents approved worldwide for clinical use (FIG. 1 and Table 1).

The major drawback of these agents is their limited sensitivity (relaxivity). The relaxivity of a contrast agent is the measure of its efficacy and usually expressed as the concentration-normalized amount of increase in the longitudinal relaxation rate $1/T_1$ per millimole of agent in the unit of $mM^{-1}\times s^{-1}$. As a result, MR imaging applications using such agents require high tissue concentrations (0.1-0.6 mM). Relaxivity of these agents drops significantly at higher magnetic fields, which makes them inefficient in the high-field MR scanners for clinical diagnostic imaging. The high-field scanners can greatly shorten data acquisition time, improve signal-to-noise ratio (SNR) and provide higher spatial resolution. Recently, the use of the $Gd^{3+}$-based MRI contrast agents has been linked to nephrogenic systemic fibrosis (NSF), an acute and fatal toxic adverse reaction in patients with impaired renal function. NSF is believed to be caused by the in vivo release of the $Gd^{3+}$ ions from the chelates. The toxicity of gadolinium stems from the fact that the ionic radius of Gd(III) (1.02 Å) is very similar to that of calcium(II) (1.00 Å). Hence, the presence of this heavy metal ion in the body can disrupt the normal functions of many types of voltage-gated $Ca^{2+}$-channels at the nano- to micro-molar concentration level. In addition to toxicity, due to the lack of ability to penetrate cells, these small molecule-based $T_1$ contrast agents function only as extracellular agents, which limits their use in detecting biological receptors or markers within the cell and makes them ineffective as cellular MR probes.

TABLE 1

Stability constants and relaxivity values for the commercial MRI contrast agents

| Trademark | $LogK_{GdL}$ | $r_1(mM^{-1}\times s^{-1})$ |
|---|---|---|
| Dotarem ® | 25.3 | 4.2 |
| ProHance ® | 23.8 | 4.4 |
| Gadovist ® | 20.8 | 5.3 |
| Magnevist ® | 22.2 | 4.3 |
| Omniscan ® | 16.8 | 4.6 |
| OptiMARK | 16.8 | 5.2 |
| MultiHance | 18.4 | 6.7 |
| Primovist | 23.5 | 7.3 |
| Vasovist | 23.2 | 19 |

All the existing $T_2$ contrast agents are based on superparamagnetic iron oxide nanoparticles (SPIOs). These agents shorten the transverse relaxation time ($T_2$) of bulk water to produce a negative or darkened contrast. Although SPIOs are nontoxic and FDA-approved contrast agents with higher sensitivity and can penetrate cells, from the standpoint of clinical diagnosis and cellular imaging, the image contrast produced by such agents is far less desirable than that by the $T_1$ agents. It is difficult to distinguish between the darkened spots produced by the accumulation of a $T_2$ agent and the signals caused by bleeding, calcification, metal deposit, or other artifacts from the background. This fact can complicate the correct interpretation of imaging results, and is a major barrier for $T_2$ agents to gain widespread clinical applications in replacement of $T_1$ agents. Besides this, imaging with $T_2$ contrast requires longer acquisition times. Currently, the primary application of SPIOs $T_2$ agents is for image-guided drug delivery and the monitoring of surgical procedures.

Besides the $Gd^{3+}$ ion of seven unpaired electrons, the next highest possible number of unpaired electrons is five (S=5/2). The electron configuration corresponding to this spin state is found in the stable transition metal ions Fe(III) and Mn(II). Although iron is an essential element in biology, the use of analogous $Fe^{3+}$-chelates to deliver Fe(III) for $T_1$ MRI contrast is deemed unacceptable due to the high cellular toxicity of this metal. Because most high-spin Fe(III) complexes have low to modest thermodynamic stability and are kinetically labile, in vivo release of free $Fe^{3+}$ ions from such chelates is inevitable. As the result, any $Fe^{3+}$-containing compound administered parenterally can disturb the iron homeostasis that is tightly regulated by ferritin and transferrin receptors in the body. The ferrous ion $Fe^{2+}$, produced from any non-sequestered ferric ion through reduction by a variety of biomolecules, can catalyze the generation of reactive oxygen species (ROS) including hydroxyl radical and peroxide radical via the so-called Fenton chemistry:

$$Fe^{2+}+H_2O_2 \rightarrow Fe^{3+}+OH.+OH^- \quad (1)$$

$$Fe^{3+}+H_2O_2 \rightarrow Fe^{2+}+OOH.+H^+ \quad (2)$$

The above ROS species can lead to wide-spread systemic injury to the liver, heart and endocrine organs as well as increases in infection. To avoid the $Fe^{3+}$ or $Fe^{2+}$ ions to be leached into the body, completely insoluble iron compounds in the form of superparamagnetic iron oxide nanoparticles (SPIOs of $Fe_3O_4$ or $\gamma$-$Fe_2O_3$) have been developed as $T_2$ MRI contrast agents (vide supra).

An FDA approved $Mn^{2+}$-based small-molecule complex has been developed as a MRI contrast agent, namely manganese dipyridoxal diphosphate (MnDPDP) for application to liver, pancreas, and heart. However, the $Mn^{2+}$ is shown to be released in vivo due to the transmetallation with zinc(II). Therefore, the contrast enhancement detected in these organs is due to the presence of the released paramagnetic $Mn^{2+}$ ions. The cellular toxicity of higher level manganese (>1 mM) has prevented any $Mn^{2+}$-complex from being developed as the generalized MRI contrast agent. It is well known that exposure to high concentration level of $Mn^{2+}$ can lead to neurological deficits, particularly a neurological disorder resembling Parkinson's disease.

SUMMARY OF THE INVENTION

This invention describes a synthetic procedure for preparing nanoparticles from a class of metal cyanide compounds whose surfaces are coated with a water-soluble and biocompatible polymer. Such nanoparticles have long blood circulation half lives, very low release of free $Mn^{+2}$ ions, very low cyanide toxicity, high relaxivity values and can be used at low and high magnetic fields as non-gadolinium containing MRI contrast agents.

A contrast agent composition, comprising a plurality of nanoparticles having the formula $A_xMn_y[M(CN)_6]_z.nH_2O$ where A=Li, Na, K, $NH_4$ or Tl; M=Cr, Mn, Fe, Co or Ru; x=0-2; y=1-4; z=1-4; and n=0 or 1-20, said nanoparticles adaptable for use as a MRI contrast agent.

A maganese(II) hexacyanometallate composition, comprising manganese(II) hexacyanometallate nanoparticles having a faced-centered cubic structure (space group $Fm3\overline{m}$) and having the unit cell parameter a=10±1 angstroms and are adaptable for use as an MRI $T_1$ contrast agent; and water.

A process for preparing a manganese(II) contrast agent composition, comprising the steps of: treating a hexacyanometallate with a H-form ion exchange resin and then mixing with manganese chloride and an organic amine or an alkali metal hydroxide or carbonate and forming a manganese(II) contrast agent.

DETAILED DESCRIPTION OF THE INVENTION

According to the concepts of the present invention, various nanosized particles containing manganese(II) ions in the crystal lattice have been developed for use as MRI contrast agents. More specifically, the contrast agents are manganese (II) hexacyanoferrate compounds having the formulas $Mn_2[Fe^{II}(CN)_6]$, $A_2Mn_3[Fe^{II}(CN)_6]_2.nH_2O$, $AMn[Fe^{III}(CN)_6].nH_2O$ where A=Li, Na, K, $NH_4$ or Tl and $Mn_3[Fe^{III}(CN)_6]_2.nH_2O$ where n=0 or 1-20. The compounds generally have the same crystal structure, that is a faced-centered cubic lattice (space group Fm $\overline{3}$ m) and the unit cell parameter a=10±1 angstroms as set forth in FIG. 2.

Figure 1:
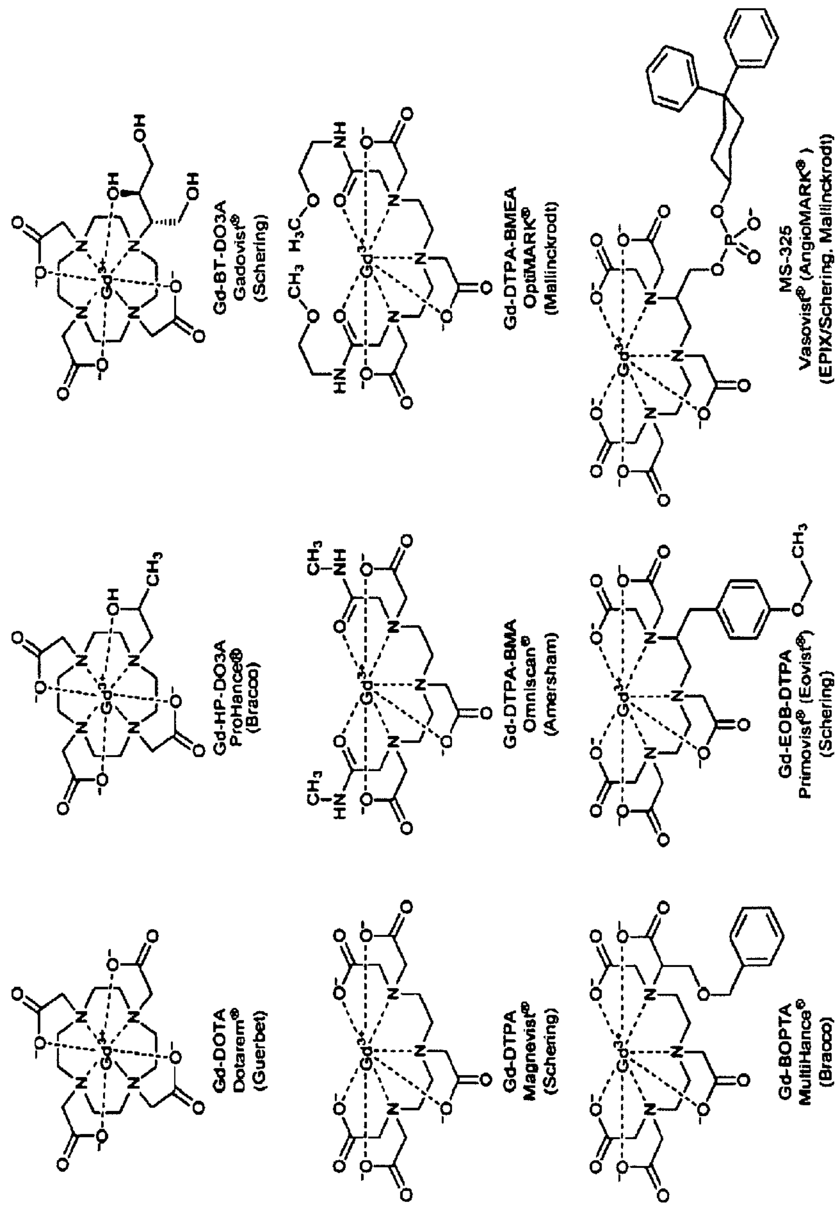
FIG. 1 relates to schematic structures of common MR contrast agents with one coordinated water molecule omitted from each structure for clarity.
Figure 2:
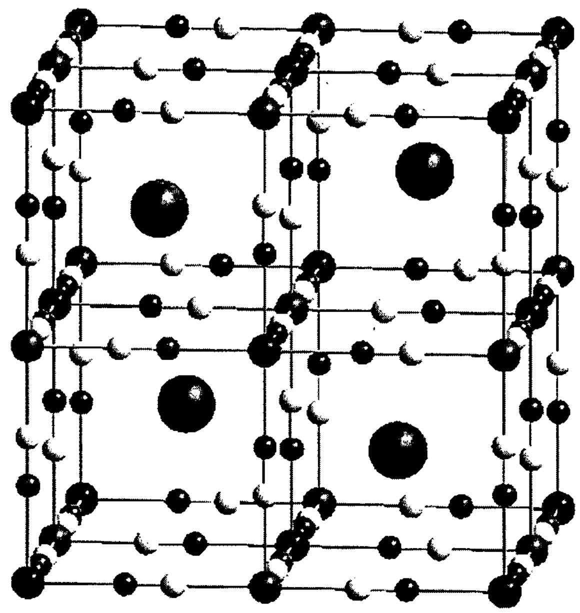
FIG. 2 is the crystal structure of $KMn[Fe^{III}(CN)6]$.

Referring to FIG. 2, due to the strong ligand-field effect and simultaneous coordination of the $CN^-$ group to both iron and manganese ions in this extended 3D coordination network structure, both metal ions and $CN^-$ ligand are completely locked in the lattice positions and generally cannot be released from the compound. A result is that very low amounts of $Mn^{2+}$ ions are released and thus the compounds there are considered stable and have very low toxicity. It has also been found that such compounds have a long blood circulation half life that allows a longer time window for imaging studies. Blood circulation half lives of the contrast agents of the present invention generally range from about 0.1 to 2 hours, desirably from about 0.25 to about 2.0 hours and preferably from about 0.5 to about 2.0 hours. Moreover, the concentrations of the manganese contrast agents in water that can be utilized for application to an animal such as a human being for an MRI analysis are amounts generally from about 1 micromole to about 150 millimoles, desirably from about 10 micromolar to about 100 millimolar and preferably from about 25 micromolar to about 50 millimolar per liter of solution.

The manganese(II) hexacyanometallate nanoparticles are made using conventional methods known to the art and to the literature, having diameters generally from about 4 to about 500 nm, desirably from about 6 to about 200 nm and preferably from about 8 to about 100 nm. The particle diameter size is important in that it results in long circulation times in the blood stream before it is removed by the body. In contrast thereto, very small diameter sizes such as less than 2 nm or less than 1 nm are avoided since they are readily removed from the human body and have a short residence time therein, for example less than 20 minutes that is unacceptable for use as a MRI contrast agent.

The manganese contrast agents of the present invention are adapted to be applied to the body as dispersed nanoparticles in a solvent such as water stabilized by a hydrophilic coating comprising a carboxylic acid or a hydrophilic biocompatible polymer, or both. The hydrophilic coating acts to make the otherwise insoluble manganese(II) nanoparticles dispersible in water, and thus promoting water stability of such nanoparticles while providing a protection shell against nanoparticle aggregation and precipitation. Suitable carboxylic acids include, but are not limited to, common carboxylic acids such as acetic acid, oxalic acid, citric acid, tartaric acid, adipic acid, gluconic acid, and other mono-, di-, tri- or polycarboxylic acids. Suitable hydrophilic biocompatible polymer used for coating to prolong blood circulation times, reduced biological toxicity, and particle solution stability against aggregation and precipitation include, but are not limited to, polyethylene glycol (PEG), chitosan, dextran, e.g., polymers of glucose having number average molecular weights up to 200,000, and polyvinylpyrrolidone (PVP).

The manganese contrast agent aqueous solutions are generally stable in acidic to neutral solutions with a pH value from about 1 to about 7.5, desirably from about 2.5 to about 7.5, and preferably from about 3.5 to about 7.3.

A general procedure for preparation of nanoparticulate $Mn_2[Fe(CN)_6]$ MRI contrast agents comprises the following reactions:

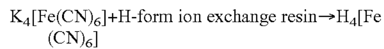

$$K_4[Fe(CN)_6]+\text{H-form ion exchange resin}\rightarrow H_4[Fe(CN)_6]$$

$$2MnCl_2+H_4[Fe(CN)_6]+\text{triethylamine}\rightarrow Mn_2[Fe(CN)_6]$$

Generally any type of known H-form ion exchange resin can be used with suitable examples including AMBERLITE™ IR120 H from Dow Chemical Company, a styrene divinylbenzene copolymer with sulfonic acid groups, AG 50W-X2 from Bio-Rad, a cation exchange resin, and AMBERLYST™ 16 West from Rohm and Hass, a sulfonic acid ion exchange resin.

With respect to the second part of the contrast agent preparation utilizing an amine, generally the suitable organic amine compounds include, but not limited to, amines having from 3 to about 12, and desirably from 3 to about 10 carbon atoms such as triethylamine, benzylamine, ethylenediamine, piperidine, pyridine, pyrazine, 2,2'-bipyridine and 4,4'-bipyridine, or any combination thereof. Alternatively, an alkali metal hydroxide AOH or alkali metal carbonate $A_2CO_3$ where A=Li, Na, K, Rb or Cs can be used in the place of the organic amine.

The manganese(II) contrast agents of the present invention can be prepared as follows:

A proper concentration, i.e. $10^{-3}$ to $10^3$ M, of $K_4[Fe(CN)_6]$ was first treated with a proper amount of H-form ion exchange resin, i.e. about 1 gram to about 1,000 grams and desirably from about 5 to about 500 grams, to yield $H_4[Fe(CN)_6]$ that was then mixed with a proper concentration, i.e. $10^{-3}$ to $10^3$ M and desirably from about 0.01 to about 1.00 M of $MnCl_2$ in the presence of a proper amount of triethylamine, i.e. 0.01 gram to 10 grams and desirably from about 0.05 to about 5.00 grams, citric acid, i.e. 0.01 gram to 10 grams, and desirably from about 0.01 to about 3.00 grams, and PVP, i.e. 0.01 gram to 10 grams and desirably from about 0.03 to about 8.00 grams, to form nanoparticles of $Mn_2[Fe(CN)_6]$ with the size ranging from 4 to about 500 nm and desirably from about 8 to about 100 nm, depending on the ratio of the reacting components. Simple reaction temperatures of the first reaction range from about 0 to about 100° C. and desirably from about 5 to about 95° C. The reaction temperature with respect to the second reaction generally range from about 0 to about 100° C. and desirably from about 5 to about 95° C. The reaction conditions are generally limited by the freezing point and boiling point of water.

When other manganese contrast agents other than $Mn_2[Fe(CN)_6]$ are desired, the process is essentially similar except that the ratios of the above noted compounds are changed. For example, if $Mn_3[Fe^{III}(CN)_6]_2$ is desired, a proper concentration, i.e. $10^{-3}$ to $10^3$ M of $K_3[Fe(CN)_6]$ can be treated with a proper amount of H-form ion exchange resin and allowed to react with a proper concentration, i.e. $10^{-3}$ to $10^3$ M and desirably from about 0.01 to about 1.00 M, of $MnCl_2$ in the molar ratio of $K_3[Fe(CN)_6]$:$MnCl_2$ to be 2:3 while all the other conditions are kept exactly the same as described in [0028]

In order to determine the release rate of the $Mn^{2+}$ ions of the manganese(II) hexacyanometallate contrast agents of the present invention, nanoparticles of the formula $Mn_2[Fe(CN)_6]$, were treated with 20 parts of a saline solution, e.g. a NaCl solution having a pH of 1, 3, 5, and 7 and incubated at room temperatures for 16 hours. The potential transmetallation reactions between the nanoparticles and solutions each containing the following ions: 1 mM $Ca^{2+}$, 1 mM $Mg^{2+}$, 1 mM $K^+$ or 1 mM $Zn^{2+}$ ions were also studied. The results were analyzed by Atomic Adsorption (AA) and showed that the highest Mn concentration found has ~19 ppm, which is much less than the minimal toxic level of 0.1 mM, see FIG. 3.

Figure 3:
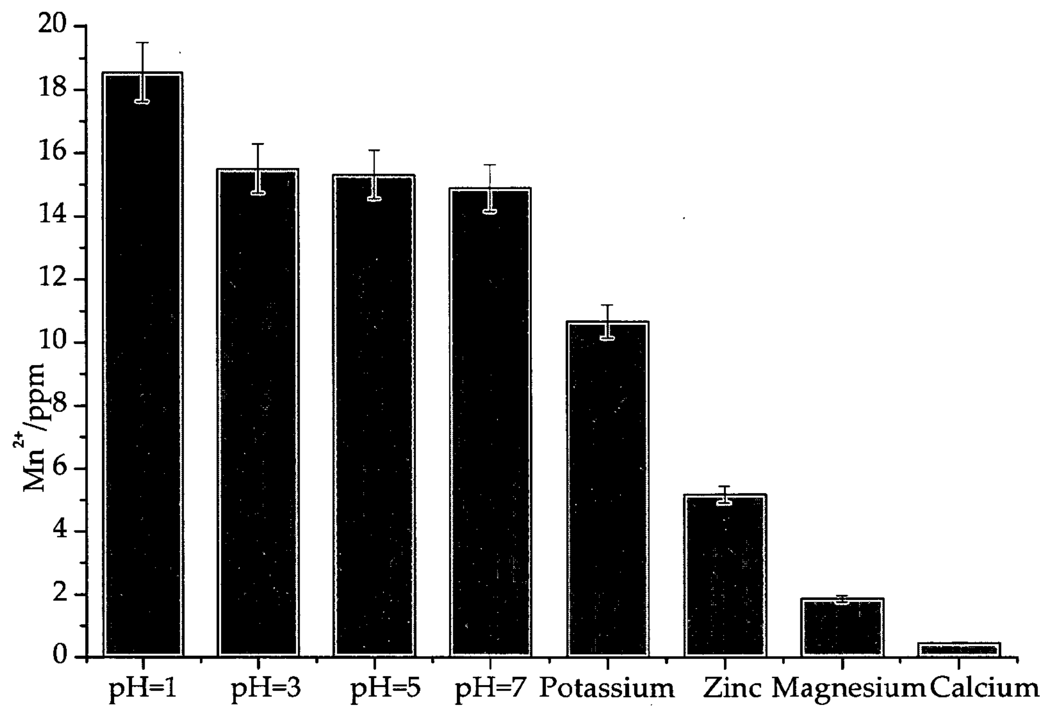
FIG. 3 is a diagram showing the $Mn^{2+}$ ion leaching results under different pH conditions.

As apparent from FIG. 3, the $Mn^{2+}$ release amounts were higher at lower pH levels and essentially nil when utilized with magnesium and calcium ions. Moreover, the release rate of the Maganese(II) hexacyanoferrate with respect to $Mn^{2+}$ is approximately 2,000 times less than the release rate of MnDPDP. Thus, release rates of at least about 25, about 50, about 100, about 500, or about 1,000 times less than the release rate of MnDPDP can be readily obtained. Stated in other words, the in vitro release rate of $Mn^{2+}$ at a pH of about 7 is from about 10 to about 20, desirably from about 12 to 18, and preferably from about 14 to about 16 parts per million in water for a 24 hour time period. FIG. 3 also shows that the release rate of manganese in the presence of other ions at a pH of 7 such as zinc, magnesium, and calcium was also extremely low.

The concentrations of free cyanide ions released from manganese(II) hexacyanoferrate MRI contrast agents of the present invention is generally at the level of ~10 ppm, which is about 10 to 15 times less than a minimum toxic level of 0.1 mM currently set forth by the EPA. That is, the in vitro concentration of free cyanide ions released by the MRI contrast agents of the present invention is generally about 2 to about 50, and desirably from about 5 to about 30 times less than the current minimum toxic EPA level of 0.1 mM of free $CN^-$ ions. These values are determined based upon the release rate of free cyanide ions in water during a 24 hour time period at room temperature, e.g. about 65 to about 85° F. The manganese contrast agents of the present invention thus essentially have no toxicity and are very safe for use in MRI scanning.

Figure 4:
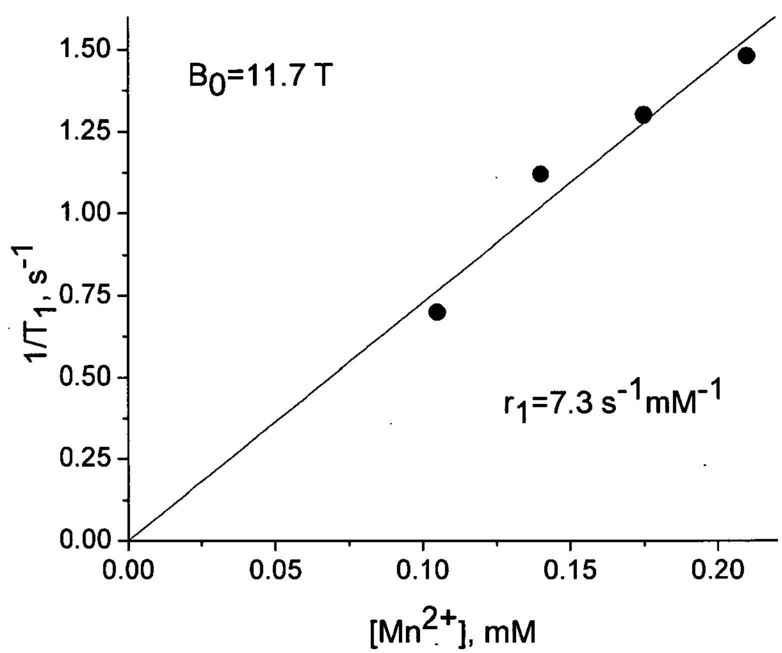
FIG. 4 shows the proton $T_1$ (top) and $T_2$ (bottom) relaxation rate versus concentration of $Mn^{2+}$ ion at 11.7 T.
Figure 4:
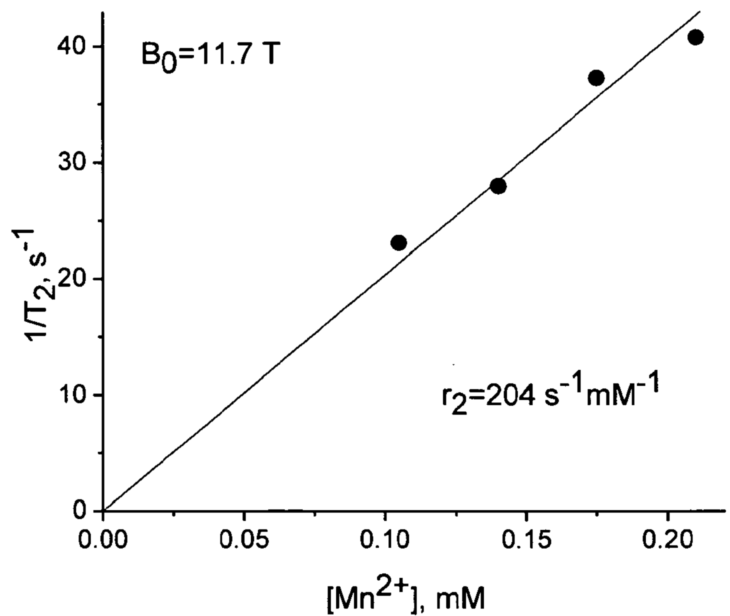

A series of proton $T_1$ and $T_2$ relaxation measurements using 500 MHz (11.7 T) NMR were made. The results expressed as the concentration-normalized relaxivity values are $r_1=7.3\ mM^{-1}\times s^{-1}$ and $r_2=204\ mM^{-1}\times s^{-1}$ per mM of $Mn^{2+}$ ions, see FIG. 4. These values are among the highest measured relaxivity values ever obtained for any MRI contrast agent.

Figure 5:
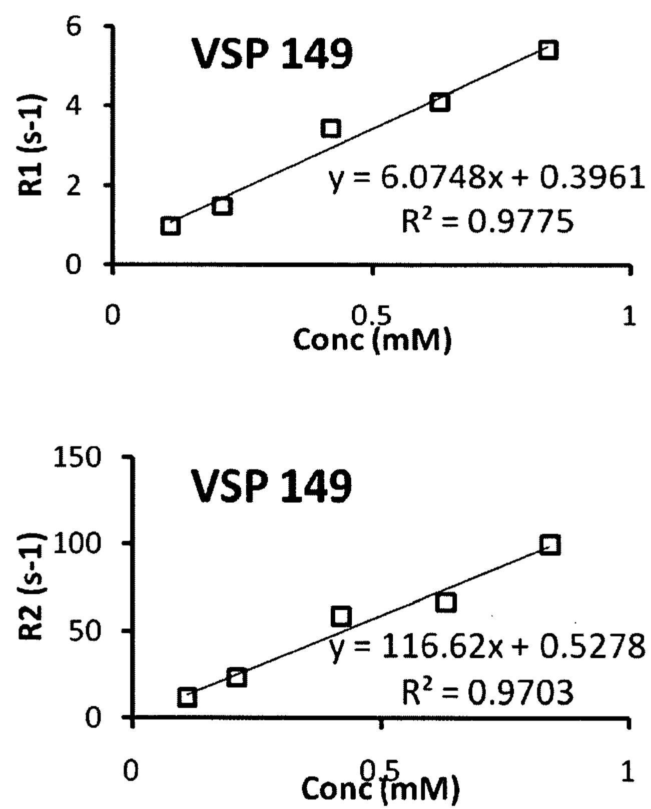
FIG. 5 shows the proton $T_1$ (top) and $T_2$ (bottom) relaxation rate versus concentration of $Mn^{2+}$ ion at 7.0 T.

Solutions of various concentrations of $Mn_2[Fe(CN)_6]$ nanoparticles were used for $T_1$ and $T_2$ Measurements using a 7.0 T MRI scanner. For $T_1$ measurements, an inversion recovery gradient echo sequence with a TE=4 ms was used. The inversion time was varied between 30-2000 ms. $T_2$ measurements were performed using a spin-echo sequence of TR of 10000 ms, and TE of 10.6-340 ms, see FIG. 5. The results expressed as the concentration-normalized relaxivity values from these measurements are $r_1=6.07\ mM^{-1}\times s^{-1}$ and $r_2=117\ mM^{-1}\times s^{-1}$ per mM of $Mn^{2+}$ ions. These results further confirmed that $Mn_2[Fe(CN)_6]$ nanoparticles possess have relaxivity values at a medically relevant high magnetic field of 7.0 Tesla.

The in vitro $T_1$ (positive contrast values) of the MRI contrast agents of the present invention have relaxivity values, i.e. $r_1$, of from about 1 to about 15, desirably from about 2 to about 15, and preferably from about 4 or about 6 to about 14 $mM^{-1}\cdot s^{-1}$/mM of $Mn^{+2}$ ions. The $T_2$ (negative contrast agents) of in vitro relaxivity values, i.e. $r_2$, is from about 50 to about 300, desirably from about 170 to about 250, and preferably from about 100 to about 200 $mM^{-1}\cdot s^{-1}$/mM of $Mn^{+2}$ ions.

Another advantage of the present invention is that the manganese MRI contrast agents can be utilized in either high or low magnetic field strength such as from about 0.5 to about 11 Tesla and desirably from about 1.0 to about 9.0 Teslas.

The manganese contrast agents of the present invention can be utilized where ever MRI contrast agents have been utilized heretofore and the same is well known to the art and to the literature including the administration thereof. The contrast agent can be utilized with respect to various animals including pets such as dogs, cats, horses, cattle, pigs, goats, chickens, turkeys, etc. A highly preferred end use is for MRI diagnosis of human beings, i.e. persons, as by various well known methods such as oral administration, intravenous injection, and the like.

While in accordance with the patent statutes the best mode and preferred embodiment have been set forth, the scope of the invention is not intended to be limited thereto, but only by the scope of the attached claims.

What is claimed is:

1. A contrast agent composition, comprising:
a solution of water and
a face-centered cubic crystal comprising:
a plurality of nanoparticles having the formula $A_xMn_y[M(CN)_6]_z \cdot nH_2O$ where A=Li, Na, K, $NH_4$ or Tl; M=Cr, Mn, Fe, Co or Ru; x=0-2; y=1-4; z=1-4; and n=0 or 1-20; said nanoparticles adaptable for use as a MRI contrast agent; wherein said nanoparticles have a diameter of from about 4 to about 500 nanometers; wherein said nanoparticles have a hydrohilic surface coating and are water soluble; wherein said nanoparticles have an in vitro release rate of 2 to 50 times less than 0.1 mM of free $CN^-$ ions in water per 24 hour period; wherein the concentration of said nanoparticles in water is from about 1 micromole to about 150 millimoles per liter of solution; and wherein said nanoparticles are adaptable for use in a magnetic field strength of from about 0.5 to about 11 Tesla; and said nanoparticles being suitable as MRI contrast agents in human and animal bloodstreams due to interactions of the paramagnetic $Mn^{2+}$ ions on the nanoparticles surfaces with the protons of water molecules in human and animal bloodstreams.

2. The contrast agent composition of claim 1, wherein said nanoparticles have an in vitro $T_1$ relativity value, $r_1$, of from about 1 to about 15 $mM^{-1} \cdot s^{-1}$/mM of $Mn^{+2}$ ions, and wherein said nanoparticles are stable in a solution having a pH value from about 1 to about 7.5.

3. The contrast agent composition of claim 2, wherein said nanoparticle diameters are from about 6 to about 200 nm, and wherein said hydrophilic coating is a carboxylic acid or a hydrophilic biocompatible polymer.

4. The contrast agent composition of claim 3, wherein said relaxivity value is from about 4 to about 14 $mM^{-1} \cdot s^{-1}$/mM of $Mn^{+2}$ ions, and wherein said nanoparticles are stable in a solution having a pH value from about 3.5 to about 7.3.

5. The contrast agent composition of claim 2, wherein said nanoparticles have the formula $A_2Mn_3[Fe^{II}(CN)_6]_2.nH_2O$, $AMn[Fe^{III}(CN)_6].nH_2O$, or $Mn_3[Fe^{III}(CN)_6]_2.nH_2O$, or any combination thereof, where A=Li, Na, K, $NH_4$ or Tl and wherein n=0 or 1-20.

6. The contrast agent composition of claim 4, wherein said nanoparticles have the formula $A_2Mn[Fe^{II}(CN)_6]_2.nH_2O$, $AMn[Fe^{III}(CN)_6].nH_2O$, or $Mn_3[Fe^{III}(CN)_6]_2.nH_2O$, or any combination thereof, where A=Li, Na, K, $NH_4$ or Tl and wherein n=0 or 1-20, and wherein said nanoparticle diameters are from about 8 to about 100 nanometers.

7. The contrast agent composition of claim 1 comprising manganese(II) hexacyanometallate nanoparticles having a faced-centered cubic structure (space group Fm3m) and having a unit cell parameter a=10±1 angstroms.

8. The contrast agent composition of claim 1, wherein said manganese hexacyanometallates comprise the formulae $A_2Mn_3[Fe^{II}(CN)_6]_2.nH_2O$, $AMn[Fe^{III}(CN)_6]nH_2O$ where A=Li, Na, K, $NH_4$ or Tl and $Mn_3[Fe^{III}(CN)_6]_2.nH_2O$ where n=0 or 1-20, or any combination thereof.

9. The contrast agent composition of claim 1, wherein the in vitro release rate of $M_n^{2+}$ in water at a pH of about 7 is from about 12 to about 18 parts per million during a 24 hour time period, and wherein said nanoparticles are coated with a hydrophilic coating.

10. The contrast agent composition of claim 1, having a relaxivity $T_1$ in vitro value, $r_1$, of from about 2 to about 15 $mM^{-1} \cdot s^{-1}$/mM of $Mn^{+2}$ ions, and wherein said hydrophilic coating is a carboxylic acid or a hydrophilic biocompatible polymer.

11. A process for preparing a manganese(II) contrast agent composition of claim 1, comprising the steps of:
treating a hexacyanometallate with a H-form ion exchange resin and then mixing with manganese chloride and an organic amine or an alkali metal hydroxide or an alkali metal carbonate in the presence of water; and forming a plurality of water soluble of manganese(II) contrast agent nanoparticles having the formula $A_xMn_y[M(CN)_6]_z.nH_2O$ where A=Li, Na, K, $NH_4$ or Tl; M=Cr, Mn, Fe, Co or Ru; x=0-2; y=1-4; z=1-4 and n=0 or 1-20.

12. The process of claim 11, wherein said manganese(II) contrast agents are in the form of hydrophilic coated nanoparticles wherein said manganese contrast agents have a diameter of from about 4 to about 500 nanometers, wherein said manganese contrast agents have an in vitro $T_1$ relaxivity, $r_1$, value of from about 1 to about 15 $mM^{-1} \cdot s^{-1}$/mM of $Mn^{+2}$ ions: wherein said manganese(II) contrast agents have an in vitro release rate of 2 to 50 times less than 0.1 mM of free $CN^-$ ions in water per 24 hour period.

13. The process of claim 12, wherein said nanoparticles are stable in a solution having a pH value of from about 1 to about 7.5; and wherein said organic amine has from 3 to about 12 carbon atoms, wherein said alkali metal of said hydroxide is lithium, sodium, or potassium, and wherein said alkali metal of said carbonate is lithium, sodium, or potassium.

14. The process of claim 13, wherein said manganese(II) contrast agent diameters are from about 6 to about 200 nm; and wherein said amine comprises triethylamine, benzylamine, ethylenediamine, piperidine, pyridine, pyrazine, 2,2'-bipyridine, or 4,4'-bipyridine, or any combination thereof.

15. The process of claim 14, wherein the concentration of said manganese(II) contrast agents in water is from about 1 micromole to about 150 millimoles per liter of solution, wherein said relaxivity value is from about 4 to about 14, and wherein said nanoparticles are stable in a solution having a pH value from about 3.5 to about 7.3.

16. The process of claim 11 including administering the Mn(II) contrast agent composition to an animal.

17. A process of claim 11 comprising the step of:
administering the contrast agent composition of claim 11 to a human being via intravenous injection.

18. A process of claim 11 comprising the step of:
administering the contrast agent composition of claim 11 to a human being via oral administration.

* * * * *